US006569308B2

(12) United States Patent
Natishan et al.

(10) Patent No.: US 6,569,308 B2
(45) Date of Patent: May 27, 2003

(54) FABRICATION OF A HIGH SURFACE AREA DIAMOND-LIKE CARBON OR DIRTY DIAMOND COATED METAL MESH FOR ELECTROCHEMICAL APPLICATIONS

(75) Inventors: Paul M. Natishan, Davidsonville, MD (US); William E. O'Grady, Hyattsville, MD (US); Patrick L. Hagans, Columbia, CT (US); Brian R. Stoner, Chapel Hill, NC (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/911,389

(22) Filed: Jul. 25, 2001

(65) Prior Publication Data
US 2002/0029977 A1 Mar. 14, 2002

Related U.S. Application Data

(63) Continuation-in-part of application No. 09/418,355, filed on Oct. 14, 1999, now Pat. No. 6,267,866.

(51) Int. Cl.[7] .............................. C25B 3/00; C25B 1/00; C25F 5/00; C30B 7/12

(52) U.S. Cl. ...................... 205/413; 205/464; 205/687; 205/688

(58) Field of Search .......................... 204/284, 290.01, 204/242; 205/413, 464, 687, 688

(56) References Cited

U.S. PATENT DOCUMENTS 5,399,247 A * 3/1995 Carey et al. ................ 204/131
5,900,127 A * 5/1999 Iida et al. ................ 204/290 F
6,267,866 B1 * 7/2001 Glesener et al. ............ 205/450

OTHER PUBLICATIONS

Glesener et al., "Fabrication of A High Surface Area Boron-–Doped Diamond Coated Tungsten Mesh for Electrochemical Applications", Materials Letters, vol. 37 (month unavailable, 1988), pp. 138–142.*

* cited by examiner

*Primary Examiner*—Edna Wong
(74) *Attorney, Agent, or Firm*—John J. Karasek; Rebecca L. Forman

(57) ABSTRACT

An electrode for electrochemical uses is made of a conductive metal mesh coated with diamond-like carbon or dirty diamond. The electrode may be used in electrochemical cell either as a cathode or as an anode, or can be used with an alternating current.

5 Claims, 1 Drawing Sheet

FABRICATION OF A HIGH SURFACE AREA DIAMOND-LIKE CARBON OR DIRTY DIAMOND COATED METAL MESH FOR ELECTROCHEMICAL APPLICATIONS

This application is a Continuation-in-Part of U.S. patent application Ser. No. 09/418,355, filed Oct. 14, 1999 now U.S. Pat. No. 6,267,866. U.S. patent application No. Ser. 09/418,355 is herein incorporated in full by reference.

BACKGROUND OF THE INVENTION

1. Field of the Invention

The present invention relates to an electrode for electrochemical uses and, more particularly, to an electrode made of metal mesh coated with diamond-like carbon or dirty diamond.

2. Description of the Related Art

In recent years, there has been an increasing interest in the electrochemical properties of diamond and boron-doped diamond coated substrates, primarily due to the excellent resistance of this material to chemical degradation and, as a result, its dimensional stability. The physical and electrochemical properties of boron-doped diamond have been described in the following patents and publications incorporated herein by reference: U.S. Pat. No. 5,399,247 to Carey; U.S. Pat. No. 5,900,127 to Iida et al; Swain, "The Electrochemical Activity of Boron-Doped Polycrystalline Diamond Thin Film Electrodes" Anal. Chem 1993, 65 pp 345–351; DeClements and Swain, "The Formation and Electrochemical Activity of Microporous Diamond Thin Film Electrodes in Concentrated KOH", J. Electrochem. Soc., Vol 144, No. 3 Mar. 1997, pp 856–866; Swain "The Susceptibility to Surface Corrosion in Acidic Fluoride Media: A Comparison of Diamond, HOPG, and Glassy Carbon Electrodes", J. Electrochem. Soc., Vol 141, No. 12, December 1994, pp 3382–3393; Tenne et al, "Efficient Electrochemical Reduction of Nitrate to Ammonia Using Conductive Diamond Film Electrodes" J. Electroanal. Chem 347 (1993) pp 409–415; Awada, "Electrodeposition of Metal Adlayers on Boron-Doped Diamond Thin-Film Electrodes" J. Electrochem Soc., Vol. 142, No. 3 March 1995, pp L42–L45; Martin et al, "Hydrogen and Oxygen Evolution on Boron-Doped Diamond Electrodes" J. Electrochem. Soc., Vol 143, No. 6, June 1996, pp L133–L136, and Glesener et al "Fabrication of High Surface Area Boron-Doped Diamond Coated Tungsten Mesh for Electrochemical Applications" Material Letters 37 (1998), pp 138–142.

SUMMARY OF THE INVENTION

It has now been discovered that diamond-like carbon or diamond with non-diamond carbon inclusions, which is also known as dirty diamond, can be used in the fabrication of a high surface area electrode. This is done by forming a coating of diamond-like carbon or dirty diamond on a conductive metal mesh substrate. The mesh structure allows for enhanced mass transport of reactants when used as an electrode in an electrochemical cell. The use of conducting metal as the material that makes up the mesh substrate improves the conductivity and energy efficiency of the electrode. The diamond-like carbon or dirty diamond coating provides for enhanced dimensional stability and corrosion resistance for the mesh structure.

A further aspect of the current invention is a method of electrochemically reducing an organic of non-organic solute in a liquid solution, by providing an electrochemical cell, which includes a liquid solution containing an organic or non-organic solute and an electrode comprising a conductive metal mesh substrate coated with diamond-like carbon or dirty diamond, then charging the electrode as a cathode, and exposing the liquid solution to the electrode.

A further aspect of the current invention is a method of electrochemically decomposing an organic of non-organic solute in a liquid solution, by providing an electrochemical cell having an electrode comprising a conductive metal mesh substrate coated with diamond-like carbon or dirty diamond, applying an alternating current to said electrode and exposing the solute to the electrode.

A further aspect of the present invention is a method of electrochemically decomposing an organic or non-organic solute in a liquid solution by providing an electrochemical cell including a liquid solution containing an organic or non-organic solute and having an electrode comprising an conductive metal mesh substrate coated with diamond-like carbon of dirty diamond and having means to expose the electrode to the liquid solution and charging the electrode as an anode.

DETAILED DESCRIPTION OF THE PREFERRED EMBODIMENT

Figure 1:
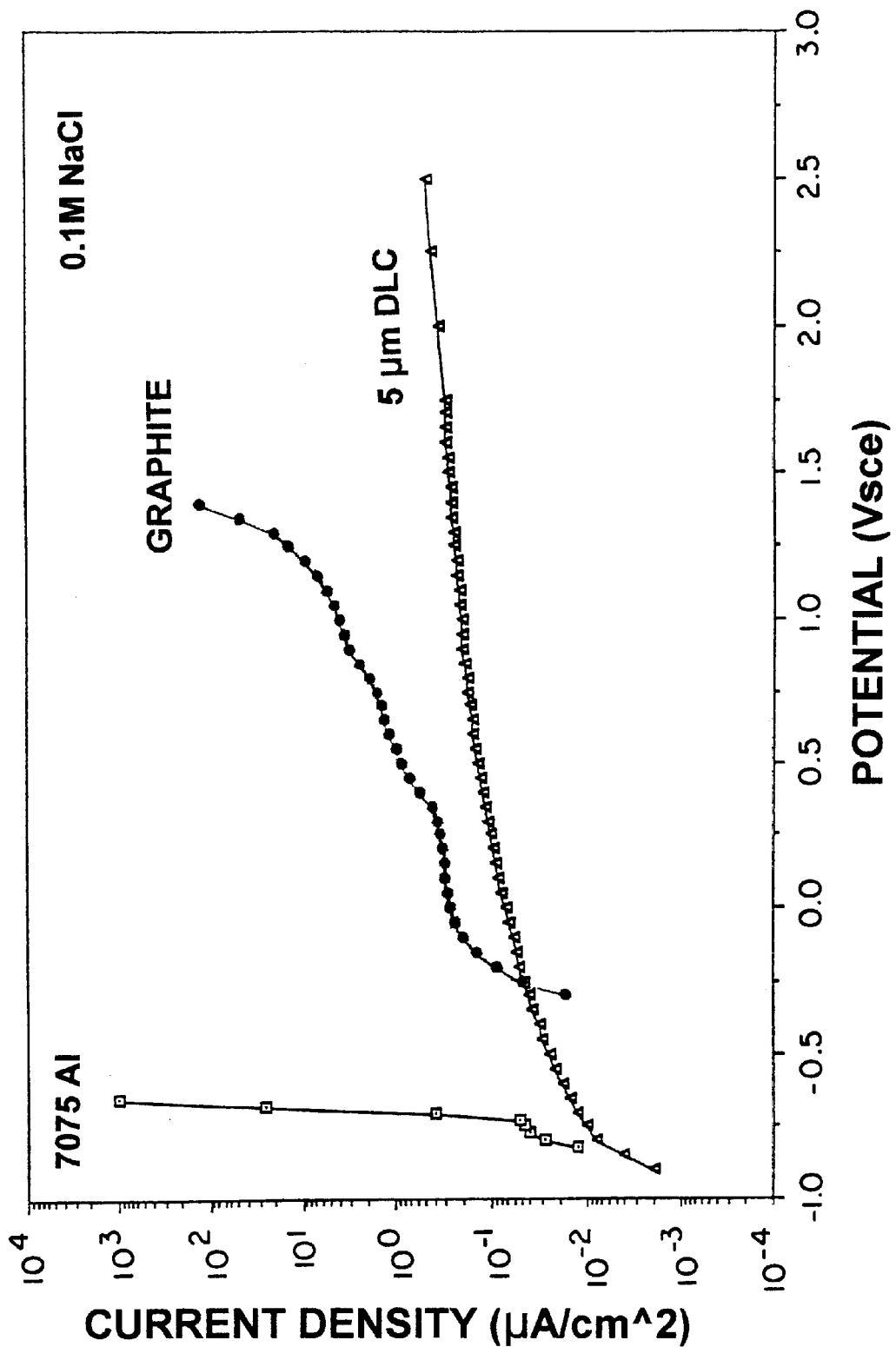
FIG. 1 shows the anodic polarization curves for Diamond-like carbon, graphite, and 7075 aluminum.

The present invention relates to the use of a diamond-like carbon or dirty diamond coated metal mesh as an electrode in electrochemical applications. The non-diamond carbon content of the coating makes the coating conductive. The conductive metal mesh of the present invention can be made of any conductive metal or alloy, including, but not limited to tungsten, titanium, tantalum, copper and alloys of these metals, other conductors, and semiconductors.

As used herein, the term "mesh" refers to a structure comprised of a grid of interwoven conductive metal filaments. The mesh morphology provides for a porous structure having a high surface area, thereby maximizing the contact of the electrode with the solution of the electrolytic cell in which the electrode is used. Preferably, the grid segments or filaments are about 0.5 mm to about 10 mm in diameter. The spacing between grid segments or filaments can range from very fine to coarse.

The conductive metal mesh may be coated with a diamond-like carbon or dirty diamond coating by any method known in the art for creating a doped diamond-like carbon or dirty diamond coating on a substrate. Preferably, the coating is formed by filament assisted chemical vapor deposition (FACVD), a method that is described, for example in the following patents and publications, incorporated herein by reference: U.S. Pat. No. 5,075,094 to Morrish et al.; U.S. Pat. No. 5,374,414 to Morrish et al; and Natishan and Morris "The Electrochemical Behavior of Diamond Coated Molybdenum", Materials Letters, Vol. 8 No. 8, August 1989, pp 269–272.

The electrode of the present invention has a wide potential window and therefore may be used in an electrochemical cell either as an anode to oxidize reactants or as a cathode to reduce reactants. Examples of reactants that can be treated include chlorides, bromides, organic materials and water. The electrode may be used for decomposition reactions or other reactions that cannot normally be run on metal electrodes. One example of would be the dehalogenation of organic materials as a reduction reaction at the cathode. The electrode may also be used with an aerated solution to produce peroxide, peroxide radicals and hydroxy radicals that, in turn, act as a reactant in the decomposition of organic materials not in contact with the diamond-like carbon or dirty diamond electrodes. Oxygen may be added at the cathode side to increase the amount of peroxide that is produced. Because of the dimensional stability of the electrode, it may be used with an alternating current to function cyclically as both an anode and a cathode. An ac signal may be desirable for some applications where a prolonged dc current could produce undesirable reactions such as a polymerization reaction.

The diamond-like carbon or dirty diamond may be further doped with boron, phosphorous, or metal.

Diamond-like carbon possesses many of the same properties as diamond, but in addition, these coatings can be deposited as smooth, amorphous coatings onto substrates at or near room temperature.

Having described the invention, the following examples are given to illustrate specific applications of the invention, including the best mode now known to perform the invention. These specific examples are not intended to limit the scope of the invention described in this application.

EXAMPLES

Diamond-like Carbon

Substrates of 7075 aluminum were cut from a ¾ inch rod and polished to a 1 $\mu$m finish. The samples were cleaned in isopropyl alcohol, placed in a deposition chamber, and etched with argon. A hydrocarbon gas was fed into the chamber and a plasma was created using a RF power supply. The deposition rate was on the order of a few microns per hour and the final diamond-like carbon (DLC) coating thickness was 5 $\mu$m.

Raman analysis of the samples was performed in air and at room temperature. The Raman spectrum obtained for the DLC coating shows broad bands at approximately 1540 and 1350 $cm^{-1}$, which are characteristic of a diamond-like or amorphous carbon film. FIG. 1 shows anodic polarization curves for DLC, 7075 aluminum, and graphite samples. Increasing current densities indicate an electrochemical reaction. The pitting potential value for 7075 aluminum is $-0.700$ $V_{sce}$. The anodic polarization curve for the 5 $\mu$m DLC showed that the coating is stable and protective to 2.5 $V_{sce}$, therefore pitting and/or general corrosion does not occur. The graphite polarization curve demonstrated that the graphite undergoes significant dissolution at potentials at and above 0.4 $V_{sce}$, whereas the DLC coating is stable to a potential of 2.5 $V_{sce}$. The polarization curve for the DLC also showed a small current density on the order of tenths of micro amps. This coating was not prepared to be electrically conductive. The DLC can be made such that it is more electrically conductive by changing the deposition conditions, thereby making the DLC coated mesh useful as an electrode for electrochemical applications. Additionally, DLC can be doped with boron, phosphorus, other metals and non-metals.

Obviously, many modifications and variations of the present invention are possible in light of the above teachings. It is therefore to be understood that, within the scope of the appended claims, the invention may be practiced otherwise than as specifically described.

What is claimed is:

1. A method of electrochemically reducing an organic or non-organic solute in a liquid solution, the method comprising the steps of:

providing an electrochemical cell including the liquid solution containing the organic or non-organic solute and an electrode comprising a conductive metal mesh substrate coated with diamond-like carbon:

connecting the electrode to a power source wherein the electrode operates as a cathode; and exposing the liquid solution to the electrode.

2. The method of claim 1 further comprising the step of:

aerating the liquid solution, thereby creating peroxide, peroxide radicals, hydroxy radicals, or combinations thereof, whereby the solute is exposed to the peroxide, peroxide radicals, hydroxy radicals or combinations thereof, and is reduced.

3. The method of claim 1 wherein the organic solute is a halogenated organic solute.

4. A method of electrochemically decomposing an organic or non-organic solute in a liquid solution, the method comprising the steps of:

providing an electrochemical cell having an electrode comprising a conductive metal mesh substrate coated with diamond-like carbon;

applying an alternating current to said electrode; and exposing the solute to the electrode.

5. A method of electrochemically decomposing an organic or non-organic solute in a liquid solution, the method comprising the steps of:

providing an electrochemical cell including the liquid solution containing the organic or non-organic solute and having an electrode comprising a conductive metal mesh substrate coated with diamond-like carbon and having means to expose the electrode to the liquid solution; and connecting the electrode to a power source wherein the electrode operates as an anode.

* * * * *